(12) United States Patent
Wang et al.

(10) Patent No.: US 11,779,666 B2
(45) Date of Patent: Oct. 10, 2023

(54) CONTINUOUS DIFFERENTIAL-PRESSURE STEAM STERILIZATION SYSTEM AND METHOD FOR A POWDER

(71) Applicant: INSTITUTE OF FOOD SCIENCE AND TECHNOLOGY, CHINESE ACADEMY OF AGRICULTURAL SCIENCES, Beijing (CN)

(72) Inventors: Fengzhong Wang, Beijing (CN); Litao Tong, Beijing (CN); Zhiying Chen, Beijing (CN); Bei Fan, Beijing (CN); Lili Wang, Beijing (CN); Long Li, Beijing (CN)

(73) Assignee: INSTITUTE OF FOOD SCIENCE AND TECHNOLOGY, CHINESE ACADEMY OF AGRICULTURAL SCIENCES, Beijing (CN)

( * ) Notice: Subject to any disclaimer, the term of this patent is extended or adjusted under 35 U.S.C. 154(b) by 0 days.

(21) Appl. No.: 18/124,582

(22) Filed: Mar. 22, 2023

(65) Prior Publication Data
US 2023/0218786 A1    Jul. 13, 2023

Related U.S. Application Data

(63) Continuation of application No. PCT/CN2022/135986, filed on Dec. 1, 2022.

(30) Foreign Application Priority Data

Dec. 14, 2021    (CN) .......................... 202111519734.7

(51) Int. Cl.
*A61L 2/00*    (2006.01)
*A23L 3/22*    (2006.01)
(Continued)

(52) U.S. Cl.
CPC ............ *A61L 2/0023* (2013.01); *A23B 9/025* (2013.01); *A23L 3/001* (2013.01); *A23L 3/003* (2013.01);
(Continued)

(58) Field of Classification Search
CPC . A61L 2/0023; A61L 2/24; A61L 2/26; A23L 3/001; A23L 3/003; A23L 3/225; A23B 9/025
See application file for complete search history.

(56) References Cited

U.S. PATENT DOCUMENTS

2011/0104006 A1*  5/2011  Kariyama ................ A23B 9/02
                                                                   422/39
2012/0186672 A1   7/2012  Fisenko et al.

FOREIGN PATENT DOCUMENTS

CN    200943609 Y    9/2007
CN    101970094 A    2/2011
(Continued)

OTHER PUBLICATIONS

Wang Shan-Shan, et al., Research Progress on Dendrobine of Medicinal Dendrobium, Food and Nutrition in China, 2020, pp. 9-15, vol. 26, No. 12.
(Continued)

*Primary Examiner* — Sean E Conley
(74) *Attorney, Agent, or Firm* — Bayramoglu Law Offices LLC (57) ABSTRACT

A continuous differential-pressure steam sterilization system for a powder, and belongs to the field of material sterilization includes: a superheated steam generation system, a steam pressure and flow rate control system, a quantitative feeding system, an instantaneous differential-pressure sterilization system, a dust explosion suppression system, a sterile cooling system, a primary gas-solid separation system, a sec-
(Continued)

ondary gas-solid separation system, a sterile storage system, a steam recovery and reheating system, and a condensate recovery system. The continuous differential-pressure steam sterilization system shortens the thermal contact time and mainly accumulates the heat on the surface of the powder, rather than in the center of the powder, which reduces the damage to the nutritional quality of the powder. Comprehensive treatment methods such as superheated steam, temperature compensation and non-sticky inner lining are adopted to reduce the problem of powder binding, agglomeration, and even blocking in the pipe of the system.

10 Claims, 2 Drawing Sheets (51) Int. Cl.
| | | |
|---|---|---|
| *A23L 3/00* | (2006.01) | |
| *B04B 11/02* | (2006.01) | |
| *B04B 11/06* | (2006.01) | |
| *B04B 13/00* | (2006.01) | |
| *A61L 2/26* | (2006.01) | |
| *A61L 2/24* | (2006.01) | |
| *A23B 9/02* | (2006.01) | |

(52) U.S. Cl.
CPC ............ *A23L 3/225* (2013.01); *A61L 2/0017* (2013.01); *A61L 2/24* (2013.01); *A61L 2/26* (2013.01); *B04B 11/02* (2013.01); *B04B 11/06* (2013.01); *B04B 13/00* (2013.01); *A61L 2202/11* (2013.01); *A61L 2202/14* (2013.01); *A61L 2202/15* (2013.01); *A61L 2202/21* (2013.01)

(56) References Cited

FOREIGN PATENT DOCUMENTS

| CN | 102151629 A | 8/2011 |
|---|---|---|
| CN | 107441519 A | 12/2017 |
| CN | 108159807 A | 6/2018 |
| CN | 110251530 A | 9/2019 |
| CN | 112547217 A | 3/2021 |

OTHER PUBLICATIONS

GB/T 8884-2007, Potato starch, China National Standards, 2007, pp. 1-6.
GB 4789.15-2016, National Food Safety Standard—Food Microbiological Examination: Enumeration of Moulds and Yeasts, China National Standards, 2016, pp. 1-5.
GB 4789.14-2014, National Food Safety Standard—Food Microbiological Examination—Bacillus Cereus, China National Standards, 2014, pp. 1-16.
GB 4789.2-2016, National food safety standard—Microbiological examination of food: Aerobic plate count, China National Standards, 2016, pp. 1-5.
GB/T 1355-1986, Wheat flour, China National Standards, 1986.
Chinese Pharmacopoeia Commission, Chuanxiong Rhizoma/Biological examination method, Pharmacopoeia of the People's Republic of China, 2020, pp. 42-43, 156-171.

* cited by examiner

CONTINUOUS DIFFERENTIAL-PRESSURE STEAM STERILIZATION SYSTEM AND METHOD FOR A POWDER

CROSS REFERENCE TO THE RELATED APPLICATIONS

This application is the continuation application of International Application No. PCT/CN2022/135986, filed on Dec. 1, 2022, which is based upon and claims priority to Chinese Patent Application No. 202111519734.7, filed on Dec. 14, 2021, the entire contents of which are incorporated herein by reference.

TECHNICAL FIELD

The present disclosure belongs to the technical field of material sterilization, and in particular, relates to a continuous differential-pressure steam sterilization system and method for a powder.

BACKGROUND

The main raw materials of instant foods, functional foods, and drugs, such as cereal powder, tea powder, traditional Chinese drug powder, and milk powder, have broad application prospects. With the continuous improvement of living standards, the demand of Chinese people for cereal powder, fruit and vegetable powder, tea powder, protein powder, and traditional Chinese drug powder has increased year by year. However, powdered foods and drugs are likely to be contaminated by microorganisms such as *Bacillus, Salmonella, Escherichia coli*, and *Aspergillus flavus* due to their rich nutritional ingredients. Even a small amount of microorganisms can cause food spoilage and foodborne diseases. In addition, in the process of pharmaceutical production, if the bacteria and mold in the traditional Chinese drug powder exceed the standard, the powder will be reprocessed or even lead to production suspension in serious cases, thus causing serious losses to the enterprise. Therefore, in order to meet the needs of consumers and industrial production, it is necessary to sterilize powdered foods and drugs.

At present, the commonly used sterilization methods for powdered foods and drugs mainly include irradiation sterilization, microwave sterilization, ozone sterilization, microbial inhibition, etc. Irradiation sterilization may cause unpleasant sensory changes to the material, and irradiated food is often rejected by consumers. The defect of microwave sterilization is uneven heating, which easily causes local overheating and deterioration. Ozone sterilization cannot achieve significant and complete sterilization. Microbial inhibition easily causes the decline of edible quality and its inhibition effect is limited.

In China, there are also studies on the applications of the sterilization of powdered foods and drugs using steam as a sterilization medium. Steam sterilization is a clean and efficient sterilization method, and it is divided into wet saturated steam sterilization and dry superheated steam sterilization according to the steam type. Wet sterilization can easily increase the moisture content of the material, thus changing the dry state of the material. Superheated steam sterilization devices are mainly divided into two types: stirring type and air-flow type. However, these sterilization devices are faced with a problem in application, that is, high-intensity steam treatment easily causes the decline of material quality, such as flavor deterioration, color deepening, and reduction of effective active ingredients, and low-intensity steam treatment cannot guarantee the sterilization effect. In addition, the heat treatment time of the existing steam sterilization devices often exceeds 5 s, or even reaches 5-10 min, resulting in a serious decline in the quality of the powder. The above problems need to be solved urgently.

In the Chinese patent application CN201710684514, the feed system uses a non-condensable gas as the transmission power. The non-condensable gas is mixed with a heating non-condensable gas to pass through a heating pipe and a pressure reducing part. The temperature of the heating non-condensable gas is reduced, thus causing condensation. The powder is easy to agglomerate after absorbing moisture. As a result, the narrow throat of the thin pipe faces the risk of being blocked. In addition, the pressure reducing part must be treated by a special non-sticky material; otherwise, it will face the risk of blocking, which is the key problem for system operation.

In Chinese patent application CN201710684514, the cooling part can reduce the temperature to below 80° C., but it will also cause the temperature of the heating non-condensable gas to reduce, thus causing condensation. In addition, the gas-solid separation system also faces the problem of material agglomeration due to moisture, and the finished product needs further drying after sterilization. Therefore, the sterilization effect of the powder material cannot be guaranteed, and the nutritional quality of the product may decline during drying. Furthermore, the drying process will increase energy consumption, which is not conducive to industrial applications.

In Chinese patent application CN201710684514, the non-condensable gas is directly separated and discharged by the gas-solid separation system after being cooled, which will cause a huge waste of resources in industrial applications.

SUMMARY

In view of the above analysis, an objective of the present disclosure is to provide a system and method for killing microorganisms and insect eggs in powdered foods and drugs. The present disclosure can kill microorganisms and insect eggs safely and quickly, with simple and convenient operation, and can realize steam recycling and condensate collection, thus achieving energy conservation and environmental protection. Another objective of the present disclosure is to reduce thermal damage to the nutritional quality and application of the material while effectively killing the microorganisms in the powder.

To achieve the above objective, the present disclosure provides the following technical solutions:

A continuous differential-pressure steam sterilization system for a powder includes:

a superheated steam generating device, where the superheated steam system includes a steam generator and a steam superheater sequentially communicated with each other;

a steam pressure and flow rate control device, where the steam pressure and flow rate control device includes a pressure reducing and stabilizing mechanism, an automatic control valve, and a flow meter; superheated steam generated by the superheated steam generating device flows through the pressure reducing and stabilizing mechanism, the automatic control valve, and the flow meter in sequence; the automatic control valve is provided with a steam flow threshold; and a control system adjusts a valve opening of the automatic control valve according to a value of the flow meter;

a first spiral closed-air aspirator, where an outlet of the first spiral closed-air aspirator and an outlet of the automatic control valve are communicated with an inlet end of a steam-powder mixing pipe; a spiral blade and a motor for driving the spiral blade are provided in a housing of the first spiral closed-air aspirator; and an outlet of the first spiral closed-air aspirator is provided with a sealing gland; and a Laval nozzle, where an inlet end of the Laval nozzle is communicated with an outlet end of the steam-powder mixing pipe; a powder output from the Laval nozzle is initially cooled by sterile air blown out by a sterile cooling mechanism); and after the initial cooling, the powder flows through a primary gas-solid separation system and a secondary gas-solid separation system in sequence;

where, steam separated by the primary gas-solid separation system is heated by a steam heater, and then enters a heating pipe of the steam-powder mixing pipe to realize temperature compensation; and the heating pipe of the steam-powder mixing pipe wraps the steam-powder mixing pipe;

In the present disclosure, the steam differential-pressure sterilization combines steam pressure and flow rate control. The present disclosure shortens the thermal contact time and mainly accumulates the heat on the surface of the powder, rather than in the center of the powder. This design reduces the damage to the nutritional quality of the powder, and realizes waste heat utilization, thus realizing energy conservation and emission reduction.

When the spiral closed-air aspirator discharges the powder, the spiral blades are rotated, so the powder enters a groove. At this time, the steam at a downstream pressure end cannot enter the feeding system due to the obstruction of other blades. When the groove with the powder is turned to a vertical downward position, it is communicated with the pressure end. Under the same pressure, the powder falls into a pipe under the action of gravity, thus realizing safe and continuous delivery of the powder into the pressure pipe.

The automatic control valve is associated with the flow meter. The system sets a target flow, and the steam control valve can automatically adjust a valve opening to achieve the target flow.

Through the two levels of gas-solid separation systems, the powder temperature is gradually dropped, and the steam is not condensed into water.

The steam separated by the primary gas-solid separation system is reheated by the steam heater, and then enters the heating pipe of the steam-powder mixing pipe to realize temperature compensation. The purpose of the design is to prevent steam from condensing into water due to heat loss after encountering the cold material, so as to prevent material agglomeration and even blocking of the pipe.

In a preferred implementation of the present disclosure, the pressure reducing and stabilizing mechanism includes a first pressure gauge, a first steam valve, a pressure reducing valve, a second steam valve, and a second pressure gauge, which are connected in sequence and connected in parallel with a bypass valve; and a steam-condensate separation system and a steam and condensate discharge valve are connected between the automatic control valve and the flow meter.

The steam and condensate discharge valve and steam-condensate separation system, as auxiliary devices, play a drainage role during system startup and shutdown to reduce the water hammer phenomenon during the heating process.

In a preferred implementation of the present disclosure, the system further includes a condensate recovery system, where the condensate recovery system comprises a recovered steam heat exchanger, a condensate recovery pipe, and a condensate filter; an outlet end of the heating pipe of the steam-powder mixing pipe is connected to the recovered steam heat exchanger through a heating pipe outlet valve of the steam-powder mixing pipe; recovered steam passes through the recovered steam heat exchanger, and returns to the steam generator through the condensate recovery pipe; and the condensate filter is connected to the condensate recovery pipe, and is located between the recovered steam heat exchanger and the steam generator.

The steam for temperature compensation of the condensate recovery system comes out of the heating pipe outlet valve of the steam-powder mixing pipe and enters the recovered steam heat exchanger to be condensed into water. The recovered condensate is filtered, purified, and supplied to the steam generator as a water source.

In a preferred implementation of the present disclosure, the system further includes an automatic explosion suppressor; the automatic explosion suppressor is provided on the steam-powder mixing pipe, and includes a flame sensor, a pressure sensor, an automatic valve, a controller, and an explosion suppressant; the flame sensor and the pressure sensor are arranged at a connection between the steam-powder mixing pipe and the automatic explosion suppressor; the explosion suppressant is provided in a cavity body of the automatic explosion suppressor, and is isolated from the steam-powder mixing pipe through the automatic valve; and the controller is signal-connected to the flame sensor, the pressure sensor and the automatic valve.

The present disclosure provides the automatic dust explosion suppression system, which improves safety. When the flame sensor and the pressure sensor sense an abnormality, a control system immediately opens the automatic valve to release the explosion suppressant, namely nitrogen gas and calcium carbonate powder, into the pipe to achieve explosion suppression, so as to avoid the occurrence or further expansion of dust explosion accidents in the pipe.

In a preferred implementation of the present disclosure, the Laval nozzle includes a main body made of food-grade stainless steel and an inner lining made of Teflon or ceramic.

The Laval nozzle includes a main body made of food-grade stainless steel and an inner lining made of Teflon or ceramic to increase the non-sticky performance, thus reducing the risk of blocking caused by the binding and accumulation of the powder at the narrow throat.

In a preferred implementation of the present disclosure, the superheated steam generating device and the steam pressure and flow rate control device are controlled such that the generated superheated steam is at 180-210° C. and under 0.2-0.6 Mpa; the steam flow threshold is set as 20-30 m/s; the steam-powder mixing pipe is 150-300 cm long, and the powder and the superheated steam are controlled to pass through the steam-powder mixing pipe within 0.05-0.15 s; and an instantaneous differential pressure of the Laval nozzle is 0.15-0.5 Mpa.

The present disclosure shortens the thermal contact time and makes the continuous high temperature time of the powder less than 0.15 s. In addition, in the present disclosure, the main heat exists on the surface of the powder, and the heat in the center of the powder is small, which reduces the damage to the nutritional quality of the powder. The superheated steam temperature control ensures instantaneous sterilization without destroying the powder nutrition. Through instantaneous differential-pressure treatment, an intracellular water molecule of a microorganism or an insect egg attached to a surface of a powder particle bursts due to vaporization.

In a preferred implementation of the present disclosure, a first centrifugal chamber and a plurality of second centrifugal chambers are provided in each of the primary gas-solid separation system and the secondary gas-solid separation system; the first centrifugal chamber is provided at a center of a cavity body of the separation system, and the second centrifugal chambers are arranged at a side wall of the cavity body and surround the first centrifugal chamber; a fluid flows through a first fluid inlet and enters the first central chamber; a top fluid outlet of the first centrifugal chamber enters a plurality of branch pipes via a fluid convergence chamber, and enters the second centrifugal chambers through second fluid inlets, respectively; and a top fluid outlet of each of the second centrifugal chambers is communicated with the cavity body.

In the present disclosure, the central centrifugal chamber and the plurality of secondary centrifugal chambers in the separation system improve the fluid separation efficiency. The central centrifugal chamber performs primary separation of relatively large particles, and the relatively large particles fall into s bottom of the cavity body due to their own weight. The upper air flow enters the secondary centrifugal chambers to separate the fine particles. The air flow enters the whole cavity body, providing the cavity body a certain pressure, which is convenient for the subsequent diversion of the pressure gas.

In a preferred implementation of the present disclosure, a distance between the first fluid inlet and a top part of the first centrifugal chamber is ½ of a distance between the first fluid inlet and a bottom part of the first centrifugal chamber; and a distance between the second fluid inlet and a top part of the second centrifugal chamber is ½ of a distance between the second fluid inlet and a bottom part of the second centrifugal chamber.

The position setting of the fluid inlet gives priority to ensuring that the fluid directly generates a cyclone after entering the cavity body and the discharged fluid rises in the center without disturbing the cyclone fluid, such that the fluid can flow freely in the centrifugal chamber.

In a preferred implementation of the present disclosure, an outlet of the primary gas-solid separation system is provided with a second spiral closed-air aspirator; an inlet of the second spiral closed-air aspirator is provided with a contact sensor; and the contact sensor is connected to a motor controller of the second spiral closed-air aspirator.

As the outlet of the primary gas-solid separation system is provided with the second spiral closed-air aspirator, it can further reduce the impact of the secondary separation system on the primary system and prevent the generation of condensate. Meanwhile, in order to ensure uniform discharge, the contact sensor controls an impeller to rotate when it senses the arrival of the powder in an impeller storage region. The contact sensor is not easy to be disturbed in the powder space, thus improving the detection accuracy.

The present disclosure further relates to a continuous differential-pressure steam sterilization method for a powder, implemented by the above system, and including the following steps:

(1) system sterilization: performing system sterilization through the superheated steam for 5-10 min, and discharging the steam through the steam and condensate discharge valve and a discharge port of the secondary gas-solid separation system;

(2) adjustment of steam parameters: superheated steam temperature: 180-210° C., superheated steam pressure: 0.2-0.6 Mpa, and steam flow rate: 20-30 m/s;

(3) feeding: feeding a powder into a feeding chute, and starting a quantitative screw feeder and the first spiral closed-air aspirator such that the powder enters a system pipe;

(4) mixing of the powder with the steam: allowing the powder entering the system pipe to be mixed with the superheated steam, and controlling the powder and the superheated steam to pass through the steam-powder mixing pipe within 0.05-0.15 s, such that a surface temperature of the powder rises rapidly;

(5) differential-pressure sterilization: allowing the powder driven by the superheated steam to enter the Laval nozzle, where at this time, a pipe pressure decreases instantaneously, and an instantaneous differential pressure reaches 0.15-0.5 MPa; through the instantaneous differential-pressure treatment, an intracellular water molecule of a microorganism or an insect egg attached to a surface of a powder particle bursts due to vaporization; and a huge expansion pressure destroys a spatial structure of protein in the microorganism or insect egg;

(6) primary cooling and separation: driving, after the instantaneous differential-pressure treatment, the sterilized powder to enter the primary gas-solid separation system through sterile cold air, where at this time, a pipe temperature initially drops to 125-155° C., such that the steam is not condensed into water, and a center temperature of the powder decreases;

(7) steam recovery and temperature compensation: heating, by the steam heater, the steam separated by the primary gas-solid separation system to 185-230° C.; and guiding the heated steam to enter the heating pipe of the steam-powder mixing pipe to realize temperature compensation;

(8) secondary cooling and separation: allowing, after the primary separation, the powder to enter a secondary cooling pipe through the second spiral closed-air aspirator, where under the cooling of sterile air, the pipe temperature drops to 50-60° C., and the center temperature of the powder is lower than the pipe temperature, thus reaching a safe temperature state to reduce thermal damage; and (9) storage: storing, after the secondary cooling and separation, the sterilized powder in a sterile storage tank.

Compared with the prior art, the present disclosure can realize at least one of the following beneficial effects:

1. Compared with other sterilization methods such as irradiation and chemical inhibition, the differential-pressure steam sterilization of the present disclosure is greener and cleaner.

2. Compared with traditional air-flow and stirring steam sterilization, the differential-pressure steam sterilization of the present disclosure shortens the thermal contact time and makes the continuous high temperature time of the powder less than 0.15 s. In addition, in the present disclosure, the main heat exists on the surface of the powder, and the heat in the center of the powder is small, which reduces the damage to the nutritional quality of the powder.

3. The present disclosure adopts comprehensive treatment methods such as superheated steam, temperature compensation and non-sticky inner lining to reduce the problem of powder binding, agglomeration, and even blocking in the pipe of the system.

4. The present disclosure provides the automatic dust explosion suppression system, which improves safety.

5. The present disclosure recovers the steam by means of condensation, purifies the recovered condensate, and supplies the purified condensate to the steam generator as a water source, which is energy-saving and environmentally friendly.

BRIEF DESCRIPTION OF THE DRAWINGS

To describe the technical solutions in embodiments of the present disclosure or in the prior art more clearly, the following briefly describes the drawings required for describing the embodiments of the present disclosure or in the prior art. Apparently, the drawings in the following description show merely some embodiments of the present disclosure, and those of ordinary skill in the art may still derive other drawings from these drawings.

REFERENCE NUMERALS 11. steam generator;
12. steam superheater;
13. pressure reducing and stabilizing mechanism (including two pressure gauges, two steam valves, a pressure reducing valve, and a bypass valve);
14. automatic control valve;
15. steam and condensate discharge valve;
16. drive steam thermometer;
17. steam-condensate separation system (including a steam-condensate separator, a stop valve, and a trap);
18. flow meter;
21. feeding chute;
22. quantitative screw feeder;
23. buffer tank;
24. first spiral closed-air aspirator;
31. thermometer of steam-powder mixing pipe;
32. automatic explosion suppressor;
33. steam-powder mixing pipe;
34. heating pipe of steam-powder mixing pipe;
4. laval nozzle;
51. sterile cooling mechanism (including a blower, a precision filter, and an air filter);
52. sterile air outlet valve;
53. primary cooling pipe thermometer;
54. primary cooling pipe pressure gauge;
55. feed valve of primary gas-solid separation system;
56. secondary cooling pipe inlet valve;
57. secondary cooling pipe thermometer;
58. feed valve of secondary gas-solid separation system;
61. primary gas-solid separation system;
62. second spiral closed-air aspirator;
63. first centrifugal chamber;
64. second centrifugal chamber;
65. fluid convergence chamber;
66. filter element;
71. secondary gas-solid separation system;
72. discharge valve of secondary gas-solid separation system;
81. sterile storage tank;
82. breather valve;
91. steam heater;
92. recovered steam thermometer;
93. heating pipe inlet valve of steam-powder mixing pipe;
94. heating pipe outlet valve of steam-powder mixing pipe;
95. condensate inlet valve of recovered steam heat exchanger;
96. condensate outlet valve of recovered steam heat exchanger;
97. recovered steam heat exchanger;
98. condensate recovery pipe; and
99. condensate filter.

DETAILED DESCRIPTION OF THE EMBODIMENTS

In order to make the objectives, technical solutions and advantages of the embodiments of the present disclosure clearer, the following clearly and completely describes the technical solutions in the embodiments of the present disclosure with reference to the drawings in the embodiments of the present disclosure. Apparently, the described embodiments are some rather than all of the embodiments of the present disclosure. All other embodiments obtained by those of ordinary skill in the art based on the embodiments of the present disclosure without creative efforts should fall within the protection scope of the present disclosure.

For ease of understanding of the embodiments of the present disclosure, some specific embodiments of the present disclosure are described in further detail below in conjunction with the drawings, and these specific embodiments do not constitute a limitation to the embodiments of the present disclosure.

Figure 1:
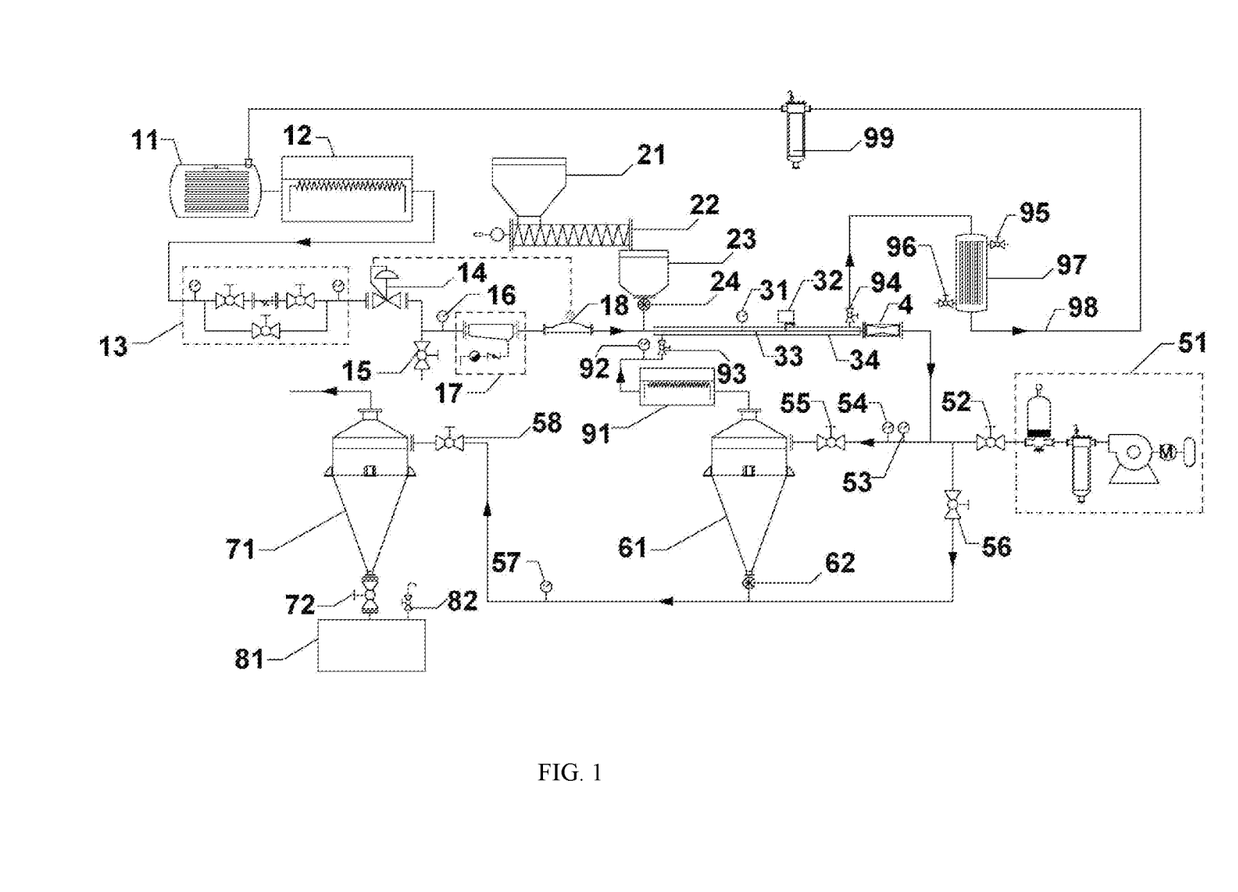
FIG. 1 is a schematic diagram of a continuous differential-pressure steam sterilization system for a powder according to the present disclosure.

As shown in FIG. 1, the present disclosure provides a continuous differential-pressure steam sterilization system for a powder, which can be used to sterilize most powdered foods and drugs. The system includes: a superheated steam generation system, a steam pressure and flow rate control system, a quantitative feeding system, an instantaneous differential-pressure sterilization system, a dust explosion suppression system, a sterile cooling mechanism, a primary gas-solid separation system, a secondary gas-solid separation system, a sterile storage system, a steam recovery and reheating system, and a condensate recovery system.

Steam generator 11 and steam superheater 12 form the superheated steam generation system.

Pressure reducing and stabilizing mechanism 13, automatic control valve 14, and flow meter 18 form the steam pressure and flow rate control system. The automatic control valve 14 is associated with the flow meter 18. The system sets a target flow, and the steam control valve can automatically adjust a valve opening to achieve the target flow. In addition, steam and condensate discharge valve 15 and steam-condensate separation system 17, as auxiliary devices, play a drainage role during system startup and shutdown to reduce the water hammer phenomenon during the heating process.

Feeding chute 21, quantitative screw feeder 22, buffer tank 23, and first spiral closed-air aspirator 24 form the quantitative feeding system. The spiral closed-air aspirator includes a motor and a transmission shaft. An output shaft of the motor is connected to the transmission shaft. An end of the transmission shaft is provided with spiral blades, and the spiral blades are located in a housing of the spiral closed-air aspirator. An outlet of the spiral closed-air aspirator is provided with a sealing gland. When the spiral blades are rotated, the powder enters a groove. At this time, the steam at a downstream pressure end cannot enter the feeding system due to the obstruction of other blades. When the groove with the powder is turned to a vertical downward position, it is communicated with the pressure end. Under the same pressure, the powder falls into a pipe under the action of gravity, thus realizing safe and continuous delivery of the powder into the pressure pipe.

Laval nozzle 4 is a main part of the instantaneous differential-pressure sterilization system. The Laval nozzle achieves instant decompression through variable-diameter throttling. The Laval nozzle has a typical variable-diameter structure with two large ends and a small center. The Laval nozzle includes a main body made of food-grade stainless steel and an inner lining made of Teflon or ceramic to increase the non-sticky performance, thus reducing the risk of blocking caused by the binding and accumulation of the powder at the narrow throat.

Automatic explosion suppressor 32 forms the dust explosion suppression system. The automatic explosion suppressor includes a flame sensor, a pressure sensor, an automatic valve, a small control system, and an explosion suppressant, etc. The flame sensor and the pressure sensor are arranged at a connection between a powder and steam heating pipe and the automatic explosion suppressor. The explosion suppressant is provided at a top center of the automatic explosion suppressor, and is isolated from the outside through the automatic valve. When the flame sensor and the pressure sensor sense an abnormality, a control system immediately opens the automatic valve to release the explosion suppressant, namely nitrogen gas and calcium carbonate powder, into the pipe to achieve explosion suppression, so as to avoid the occurrence or further expansion of dust explosion accidents in the pipe.

A blower, an air filter, and a precision filter form the sterile cooling mechanism 51. The filter is configured to prevent secondary contamination of the sterilized powder by microorganisms in the air.

A primary centrifugal separator and second spiral closed-air aspirator 62 form the primary gas-solid separation system 61.

A secondary centrifugal separator and discharge valve 72 of the secondary gas-solid separation system form the secondary gas-solid separation system 71.

Figure 2:
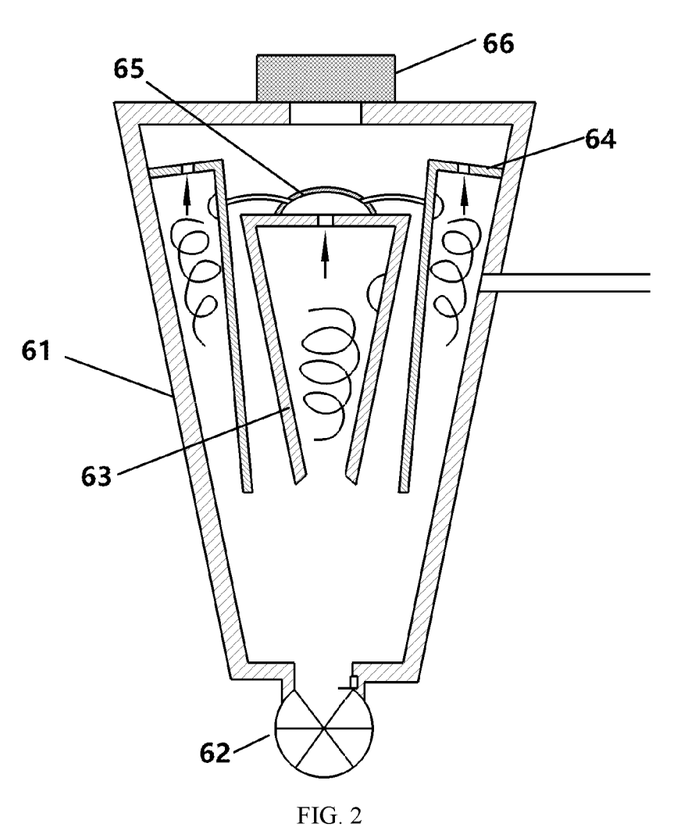
FIG. 2 is a schematic diagram of a gas-solid separation system according to the present disclosure.

Referring to FIG. 2, first centrifugal chamber 63 and a plurality of second centrifugal chambers 64 are provided in each of the primary gas-solid separation system 61 and the secondary gas-solid separation system 71. The first centrifugal chamber is provided at a center of a cavity body of the separation system, and the second centrifugal chambers are arranged at a side wall of the cavity body and surround the first centrifugal chamber. A top fluid outlet of the first centrifugal chamber enters a plurality of branch pipes via fluid convergence chamber 65, and enters the second centrifugal chambers through second fluid inlets, respectively. A top fluid outlet of each of the second centrifugal chambers is communicated with the cavity body.

Finally, the fluid is filtered through filter element 66 and discharged from the separation system.

In the present disclosure, the central centrifugal chamber and the plurality of secondary centrifugal chambers in the separation system improve the fluid separation efficiency. The central centrifugal chamber performs primary separation of relatively large particles, and the relatively large particles fall into s bottom of the cavity body due to their own weight. The upper air flow enters the secondary centrifugal chambers to separate the fine particles. The air flow enters the whole cavity body, providing the cavity body a certain pressure, which is convenient for the subsequent diversion of the pressure gas.

A distance between the first fluid inlet and a top part of the first centrifugal chamber is ½ of a distance between the first fluid inlet and a bottom part of the first centrifugal chamber. A distance between the second fluid inlet and a top part of the second centrifugal chamber is ½ of a distance between the second fluid inlet and a bottom part of the second centrifugal chamber.

The position setting of the fluid inlet gives priority to ensuring that the fluid directly generates a cyclone after entering the cavity body and the discharged fluid rises in the center without disturbing the cyclone fluid, such that the fluid can flow freely in the centrifugal chamber.

An outlet of the primary gas-solid separation system is provided with the second spiral closed-air aspirator 62. An inlet of the second spiral closed-air aspirator is provided with a contact sensor. The contact sensor is connected to a motor controller of the second spiral closed-air aspirator.

As the outlet of the primary gas-solid separation system is provided with the second spiral closed-air aspirator, it can further reduce the impact of the secondary separation system on the primary system and prevent the generation of condensate. Meanwhile, in order to ensure uniform discharge, the contact sensor controls an impeller to rotate when it senses the arrival of the powder in an impeller storage region. The contact sensor is not easy to be disturbed in the powder space, thus improving the detection accuracy.

Sterile storage tank 81 and breather valve 82 form the sterile storage system.

Steam heater 91 and recovered steam thermometer 92 form the steam recovery and reheating system. The primary gas-solid separation system separates the powder from the steam. The separated steam is reheated by the steam heater, and then enters the heating pipe 34 of the steam-powder mixing pipe to realize temperature compensation. The purpose of the design is to prevent steam from condensing into water due to heat loss after encountering the cold material, so as to prevent material agglomeration and even blocking of the pipe.

Condensate inlet valve 95 of a recovered steam heat exchanger, condensate outlet valve 96 of the recovered steam heat exchanger, the recovered steam heat exchanger 97, condensate recovery pipe 98, and condensate filter 99 form the condensate recovery system. The steam for temperature compensation comes out of the heating pipe outlet valve 94 of the steam-powder mixing pipe and enters the recovered steam heat exchanger 97 to be condensed into water. The recovered condensate is filtered, purified, and supplied to the steam generator as a water source.

Specifically, the present disclosure further relates to a continuous differential-pressure steam sterilization method for a powder, implemented by the system.

The method includes the following steps:

(1) System sterilization. The steam generator 11, the steam superheater 12, and a valve-pipe connection system are started. The whole system is subjected to steam sterilization through superheated steam for 5-10 min. The steam is discharged through the steam and condensate discharge valve 15 and a discharge port of the secondary gas-solid separation system 71.

(2) Adjustment of steam parameters. The steam superheater 12, the automatic control valve 14, and the pressure reducing and stabilizing mechanism 13 are adjusted to obtain target steam parameters, including superheated steam temperature: 180-210° C., superheated steam pressure: 0.2-0.6 Mpa, and steam flow rate: 20-30 m/s.

(3) Feeding. A powder is fed into the feeding chute 21, and the quantitative screw feeder 22 and the first spiral closed-air aspirator 24 are started, such that the powder enters a system pipe.

(4) Mixing of the powder with the steam. After entering the pipe, the powder is mixed with the superheated steam. The steam and the powder are mixed at a 150-300 cm long pipe, and the powder and the superheated steam are controlled to pass through the mixing pipe within 0.05-0.15 s. A surface temperature of the powder rises rapidly.

(5) Differential-pressure sterilization. The powder is driven by the superheated steam to enter the Laval nozzle 4. At this time, a pipe pressure decreases instantaneously. Through instantaneous differential-pressure treatment, an intracellular water molecule of a microorganism or an insect egg attached to a surface of a powder particle bursts due to vaporization, and a huge expansion pressure destroys a spatial structure of protein in the microorganism or insect egg. An instantaneous differential-pressure is 0.15-0.5 Mpa.

(6) Primary cooling and separation. After instantaneous differential-pressure sterilization, the powder is driven by sterile cold air to enter the primary centrifugal separator. At this time, a pipe temperature initially drops to 125-155° C., such that the steam is not condensed into water, and a center temperature of the powder decreases. A primary cooling pipe is 50-200 cm long.

(7) Steam recovery and temperature compensation. The steam separated by the primary gas-solid separation system 61 is heated to 185-230° C. by the steam heater 91, and enters the heating pipe 34 of the steam-powder mixing pipe to realize temperature compensation.

(8) Secondary cooling and separation. After the primary separation, the powder enters a secondary cooling pipe through the second spiral closed-air aspirator 62. Under the cooling of sterile air, the pipe temperature drops to 50-60° C., and the center temperature of the powder is lower than the pipe temperature, thus reaching a safe temperature state to reduce thermal damage.

(9) Storage. After the secondary cooling and separation, the sterilized powder is stored in the sterile storage tank 81.

The implementation effects of the present disclosure will be described below with reference to three examples.

Example 1

(1) System sterilization. The steam generator 11, the steam superheater 12, and a valve-pipe connection system are started. The whole system is subjected to steam sterilization through superheated steam for 5 min. The steam is discharged through the steam and condensate discharge valve 15 and a discharge port of the secondary gas-solid separation system 71.

(2) Adjustment of steam parameters. The steam superheater 12, the automatic control valve 14, and the pressure reducing and stabilizing mechanism 13 are adjusted to obtain target steam parameters, including superheated steam temperature: 190° C., superheated steam pressure: 0.3 Mpa, and steam flow rate: 20 m/s.

(3) Feeding. A wheat flour is fed into the feeding chute 21, and the quantitative screw feeder 22 and the first spiral closed-air aspirator 24 are started, such that the wheat flour enters a system pipe.

(4) Mixing of the wheat flour with the steam. After entering the pipe, the wheat flour is mixed with the superheated steam. The steam and the wheat flour are mixed at a 200 cm long pipe, and the wheat flour and the superheated steam are controlled to pass through the mixing pipe within 0.1 s. A surface temperature of the wheat flour rises rapidly, and the steam-powder mixing pipe is at 185° C.

(5) Differential-pressure sterilization. The wheat flour is driven by the superheated steam to enter the Laval nozzle 4. At this time, a pipe pressure decreases instantaneously, and an instantaneous differential-pressure is 0.25 Mpa.

(6) Primary cooling and separation. After instantaneous differential-pressure sterilization, the wheat flour is driven by sterile cold air to enter the primary centrifugal separator. At this time, a pipe temperature initially drops to 130° C., and a primary cooling pipe is 150 cm long.

(7) Steam recovery and temperature compensation. The steam separated by the primary gas-solid separation system 61 is heated to 200° C. by the steam heater 91, and enters the heating pipe 34 of the steam-powder mixing pipe to realize temperature compensation.

(8) Secondary cooling and separation. After the primary separation, the wheat flour enters a secondary cooling pipe through the second spiral closed-air aspirator 62. Under the cooling of sterile air, the pipe temperature drops to 58° C.

(9) Storage. After the secondary cooling and separation, the sterilized wheat flour is stored in the sterile storage tank 81.

A quality test of the sterilized wheat flour obtained in Example 1 is shown in Table 1

TABLE 1

| Test items and test bases | Total number of colonies (cfu/g) GB4789.2-2016 | Mold and yeast count (cfu/g) GB4789.15-2016 | *Bacillus cereus* count (cfu/g) GB4789.14-2014 | Smell GB1355-1986 | Appearance GB1355-1986 |
|---|---|---|---|---|---|
| Before sterilization | $3.2 \times 10^4$ | $8.6 \times 10^2$ | $1.8 \times 10^2$ | Normal | Light white |
| Example 1 | <100 | <10 | <10 | Normal | Light white |
| Comparative Example 1 | <100 | <10 | <10 | Strong burnt smell | Tawny |
| Comparative Example 2 | $1.3 \times 10^3$ | 34 | 15 | Normal | Light white |

*Note:
In Comparative Example 1, the wheat flour was subjected to 800 W microwave sterilization for 60 s; and in Comparative Example 2, the wheat flour was subjected to 2 kGy electron-beam irradiation sterilization.

It can be seen from Table 1 that the differential-pressure steam sterilization system and method of the present disclosure can effectively sterilize the wheat flour while retaining the normal smell and appearance quality of the wheat flour. The microwave sterilization of Comparative Example 1 caused deterioration of the smell and appearance of the wheat flour. The electron-beam irradiation sterilization in Comparative Example 2 did not achieve effective sterilization of the wheat flour.

Example 2

(1) System sterilization. The steam generator 11, the steam superheater 12, and a valve-pipe connection system are started. The whole system is subjected to steam sterilization through superheated steam for 8 min. The steam is discharged through the steam and condensate discharge valve 15 and a discharge port of the secondary gas-solid separation system 71.

(2) Adjustment of steam parameters. The steam superheater 12, the automatic control valve 14, and the pressure reducing and stabilizing mechanism 13 are adjusted to obtain target steam parameters, including superheated steam temperature: 180° C., superheated steam pressure: 0.25 Mpa, and steam flow rate: 25 m/s.

(3) Feeding. A Chuanxiong rhizome powder is fed into the feeding chute 21, and the quantitative screw feeder 22 and the first spiral closed-air aspirator 24 are started, such that the Chuanxiong rhizome powder enters a system pipe.

(4) Mixing of the wheat flour with the steam. After entering the pipe, the Chuanxiong rhizome powder is mixed with the superheated steam. The steam and the Chuanxiong rhizome powder are mixed at a 200 cm long pipe, and the Chuanxiong rhizome powder and the superheated steam are controlled to pass through the mixing pipe within 0.08 s. A surface temperature of the Chuanxiong rhizome powder rises rapidly, and the steam-powder mixing pipe is at 177° C.

(5) Differential-pressure sterilization. The Chuanxiong rhizome powder is driven by the superheated steam to enter the Laval nozzle 4. At this time, a pipe pressure decreases instantaneously, and an instantaneous differential-pressure is 0.2 Mpa.

(6) Primary cooling and separation. After instantaneous differential-pressure sterilization, the Chuanxiong rhizome powder is driven by sterile cold air to enter the primary centrifugal separator. At this time, a pipe temperature initially drops to 125° C., and a primary cooling pipe is 150 cm long.

(7) Steam recovery and temperature compensation. The steam separated by the primary gas-solid separation system 61 is heated to 195° C. by the steam heater 91, and enters the heating pipe 34 of the steam-powder mixing pipe to realize temperature compensation.

(8) Secondary cooling and separation. After the primary separation, the Chuanxiong rhizome powder enters a secondary cooling pipe through the second spiral closed-air aspirator 62. Under the cooling of sterile air, the pipe temperature drops to 56° C.

(9) Storage. After the secondary cooling and separation, the sterilized Chuanxiong rhizome powder is stored in the sterile storage tank 81.

A quality test of the sterilized Chuanxiong rhizome powder obtained in Example 2 is shown in Table 2.

TABLE 2

| Test items and test bases | Total number of colonies (cfu/g) Chinese Pharmacopoeia | Ferulic acid content (mg/g) Chinese Pharmacopoeia | Color Chinese Pharmacopoeia | Appearance state — |
|---|---|---|---|---|
| Before sterilization | $6.1 \times 10^4$ | 1.0702 | Pale yellow | Powdery |
| Example 2 | <100 | 0.9721 | Pale yellow | Powdery |
| Comparative Example 3 | <100 | 0.1518 | Yellowish-brown | Agglomerated |

*Note:
In Comparative Example 3, the Chuanxiong rhizome powder was subjected to moist heat sterilization at 126° C. for 15 min.

It can be seen from Table 2 that the differential-pressure steam sterilization system and method of the present disclosure can effectively sterilize the Chuanxiong rhizome powder while ensuring a small loss in the content of ferulic acid, with a loss rate of 9.17%. Although the moist heat sterilization in Comparative Example 3 achieved effective sterilization, the color of the Chuanxiong rhizome powder was deepened and the Chuanxiong rhizome powder was agglomerated, thus affecting the usability. In addition, in the comparative example, the content of ferulic acid decreased to 0.1518 mg/g, with a loss rate of 85.82%.

Example 3

(1) System sterilization. The steam generator 11, the steam superheater 12, and a valve-pipe connection system are started. The whole system is subjected to steam sterilization through superheated steam for 10 min. The steam is discharged through the steam and condensate discharge valve 15 and a discharge port of the secondary gas-solid separation system 71.

(2) Adjustment of steam parameters. The steam superheater 12, the automatic control valve 14, and the pressure reducing and stabilizing mechanism 13 are adjusted to obtain target steam parameters, including superheated steam temperature: 205° C., superheated steam pressure: 0.45 Mpa, and steam flow rate: 30 m/s.

(3) Feeding. A potato starch is fed into the feeding chute 21, and the quantitative screw feeder 22 and the first spiral closed-air aspirator 24 are started, such that the potato starch enters a system pipe.

(4) Mixing of the potato starch with the steam. After entering the pipe, the potato starch is mixed with the superheated steam. The steam and the potato starch are mixed at a 200 cm long pipe, and the potato starch and the superheated steam are controlled to pass through the mixing pipe within 0.067 s. A surface temperature of the potato starch rises rapidly, and the steam-powder mixing pipe is at 200° C.

(5) Differential-pressure sterilization. The potato starch is driven by the superheated steam to enter the Laval nozzle 4. At this time, a pipe pressure decreases instantaneously, and an instantaneous differential-pressure is 0.35 Mpa.

(6) Primary cooling and separation. After instantaneous differential-pressure sterilization, the potato starch is driven by sterile cold air to enter the primary centrifugal separator. At this time, a pipe temperature initially drops to 132° C., and a primary cooling pipe is 150 cm long.

(7) Steam recovery and temperature compensation. The steam separated by the primary gas-solid separation system 61 is heated to 220° C. by the steam heater 91, and enters the heating pipe 34 of the steam-powder mixing pipe to realize temperature compensation.

(8) Secondary cooling and separation. After the primary separation, the potato starch enters a secondary cooling pipe through the second spiral closed-air aspirator 62. Under the cooling of sterile air, the pipe temperature drops to 59° C.

(9) Storage. After the secondary cooling and separation, the sterilized potato starch is stored in the sterile storage tank 81.

A quality test of the sterilized potato starch obtained in Example 3 is shown in Table 3.

TABLE 3

| Test items and test bases | Total number of colonies (cfu/g) GB4789.2-2016 | Mold and yeast count (cfu/g) GB4789.15-2016 | Starch viscosity (BU) GB8884-2007 | Smell GB8884-2007 |
|---|---|---|---|---|
| Before sterilization | $1.8 \times 10^4$ | $4.6 \times 10^2$ | 1395 | no peculiar smell |
| Example 3 | <100 | <10 | 1360 | no peculiar smell |
| Comparative Example 4 | 450 | 61 | 1072 | no peculiar smell |

*Note:
In Comparative Example 4, the potato starch was subjected to continuous ozone treatment for 20 min.

It can be seen from Table 3 that the differential-pressure steam sterilization system and method of the present disclosure can effectively sterilize the potato starch while ensuring little difference in the starch viscosity before and after sterilization. The ozone treatment in Comparative Example 4 removed certain microorganisms in the potato starch, but the sterilization effect was not as good as that in Comparative Example 3. In addition, after the ozone treatment, the starch viscosity decreased, thus affecting the usability.

The objectives, technical solutions, and beneficial effects of the present disclosure are further described in detail in the above specific implementations. It should be understood that the above described are merely specific implementations of the present disclosure, and are not intended to limit the protection scope of the present disclosure. Any modification, equivalent replacement or improvement made within the spirit and principle of the present disclosure should fall within the protection scope of the present disclosure.

What is claimed is:

1. A continuous differential-pressure steam sterilization system for a powder, comprising:
    a superheated steam generating device, wherein the superheated steam generating device comprises a steam generator and a steam superheater sequentially communicated with each other;
    a steam pressure and flow rate control device, wherein the steam pressure and flow rate control device comprises a pressure reducing and stabilizing mechanism, an automatic control valve, and a flow meter; superheated steam generated by the superheated steam generating device flows through the pressure reducing and stabilizing mechanism, the automatic control valve, and the flow meter in sequence; the automatic control valve is provided with a steam flow threshold; and a control system adjusts a valve opening of the automatic control valve according to a value of the flow meter;
    a first spiral closed-air aspirator, wherein an outlet of the first spiral closed-air aspirator and an outlet of the automatic control valve are communicated with an inlet end of a steam-powder mixing pipe; a spiral blade and a motor for driving the spiral blade are provided in a housing of the first spiral closed-air aspirator; and an outlet of the first spiral closed-air aspirator is provided with a sealing gland; and
    a Laval nozzle, wherein an inlet end of the Laval nozzle is communicated with an outlet end of the steam-powder mixing pipe; the powder output from the Laval nozzle is initially cooled by sterile air blown out by a sterile cooling mechanism; and after the initial cooling, the powder flows through a primary gas-solid separation system and a secondary gas-solid separation system in sequence;
    wherein steam separated by the primary gas-solid separation system is heated by a steam heater, and then enters a heating pipe of the steam-powder mixing pipe to realize temperature compensation; and the heating pipe of the steam-powder mixing pipe wraps the steam-powder mixing pipe;
    the superheated steam generating device and the steam pressure and flow rate control device are controlled such that the generated superheated steam is at 180-210° C. and under 0.2-0.6 Mpa; the steam flow threshold is set as 20-30 m/s; the steam-powder mixing pipe is 150-300 cm long, and the powder and the superheated steam are controlled to pass through the steam-powder mixing pipe within 0.05-0.15 s; and an instantaneous differential pressure of the Laval nozzle is 0.15-0.5 Mpa;
    a first centrifugal chamber and a plurality of second centrifugal chambers are provided in each of the primary gas-solid separation system and the secondary gas-solid separation system; the first centrifugal chamber is provided at a center of a cavity body of the separation system, and the second centrifugal chambers are arranged at a side wall of the cavity body and surround the first centrifugal chamber; a fluid flows through a first fluid inlet and enters the first central chamber; a top fluid outlet of the first centrifugal chamber enters a plurality of branch pipes via a fluid convergence chamber, and enters the second centrifugal chambers through second fluid inlets, respectively; and a top fluid outlet of each of the second centrifugal chambers is communicated with the cavity body; and
    a distance between the first fluid inlet and a top part of the first centrifugal chamber is ½ of a distance between the first fluid inlet and a bottom part of the first centrifugal chamber; and a distance between the second fluid inlet and a top part of the second centrifugal chamber is ½ of a distance between the second fluid inlet and a bottom part of the second centrifugal chamber.

2. The continuous differential-pressure steam sterilization system for the powder according to claim 1, wherein the pressure reducing and stabilizing mechanism comprises a first pressure gauge, a first steam valve, a pressure reducing valve, a second steam valve, and a second pressure gauge, which are connected in sequence and connected in parallel with a bypass valve; and a steam-condensate separation system and a steam and condensate discharge valve are connected between the automatic control valve and the flow meter.

3. The continuous differential-pressure steam sterilization system for the powder according to claim 1, further comprising a condensate recovery system, wherein the condensate recovery system comprises a recovered steam heat exchanger, a condensate recovery pipe, and a condensate filter; an outlet end of the heating pipe of the steam-powder mixing pipe is connected to the recovered steam heat exchanger through a heating pipe outlet valve of the steam-powder mixing pipe; recovered steam passes through the recovered steam heat exchanger, and returns to the steam generator through the condensate recovery pipe; and the condensate filter is connected to the condensate recovery pipe, and is located between the recovered steam heat exchanger and the steam generator.

4. The continuous differential-pressure steam sterilization system for the powder according to claim 1, wherein the Laval nozzle comprises a main body made of food-grade stainless steel and an inner lining made of Teflon or ceramic.

5. The continuous differential-pressure steam sterilization system for the powder according to claim 1, wherein an outlet of the primary gas-solid separation system is provided with a second spiral closed-air aspirator; an inlet of the second spiral closed-air aspirator is provided with a contact sensor; and the contact sensor is connected to a motor controller of the second spiral closed-air aspirator.

6. A continuous differential-pressure steam sterilization method for a powder, implemented by the continuous differential-pressure steam sterilization system for the powder according to claim 1, and comprising the following steps:
  (1) system sterilization: performing system sterilization through the superheated steam for 5-10 min, and discharging the steam through a steam and condensate discharge valve and a discharge port of the secondary gas-solid separation system;
  (2) adjustment of steam parameters: superheated steam temperature: 180-210° C., superheated steam pressure: 0.2-0.6 Mpa, and steam flow rate: 20-30 m/s;
  (3) feeding: feeding the powder into a feeding chute, and starting a quantitative screw feeder and the first spiral closed-air aspirator such that the powder enters a system pipe;
  (4) mixing of the powder with the steam: allowing the powder entering the system pipe to be mixed with the superheated steam, and controlling the powder and the superheated steam to pass through the steam-powder mixing pipe within 0.05-0.15 s, such that a surface temperature of the powder rises rapidly;
  (5) differential-pressure sterilization: allowing the powder driven by the superheated steam to enter the Laval nozzle, wherein at this time, a pipe pressure decreases instantaneously, and an instantaneous differential pressure reaches 0.15-0.5 MPa; through the instantaneous differential-pressure treatment, an intracellular water molecule of a microorganism or insect egg attached to a surface of a powder particle bursts due to vaporization; and a huge expansion pressure destroys a spatial structure of protein in the microorganism or insect egg;
  (6) primary cooling and separation: driving, after the instantaneous differential-pressure treatment, the sterilized powder to enter the primary gas-solid separation system through sterile cold air, wherein at this time, a pipe temperature initially drops to 125-155° C., such that the steam is not condensed into water, and a center temperature of the powder decreases;
  (7) steam recovery and temperature compensation: heating, by the steam heater, the steam separated by the primary gas-solid separation system to 185-230° C.; and guiding the heated steam to enter the heating pipe of the steam-powder mixing pipe to realize temperature compensation;
  (8) secondary cooling and separation: allowing, after the primary separation, the powder to enter a secondary cooling pipe through a second spiral closed-air aspirator, wherein under a cooling of sterile air, the pipe temperature drops to 50-60° C., and the center temperature of the powder is lower than the pipe temperature, thus reaching a safe temperature state to reduce thermal damage; and
  (9) storage: storing, after the secondary cooling and separation, the sterilized powder in a sterile storage tank.

7. The continuous differential-pressure steam sterilization method for the powder according to claim 6, wherein in the continuous differential-pressure steam sterilization system for the powder, the pressure reducing and stabilizing mechanism comprises a first pressure gauge, a first steam valve, a pressure reducing valve, a second steam valve, and a second pressure gauge, which are connected in sequence and connected in parallel with a bypass valve; and a steam-condensate separation system and the steam and condensate discharge valve are connected between the automatic control valve and the flow meter.

8. The continuous differential-pressure steam sterilization method for the powder according to claim 6, wherein the continuous differential-pressure steam sterilization system for the powder further comprises a condensate recovery system, wherein the condensate recovery system comprises a recovered steam heat exchanger, a condensate recovery pipe, and a condensate filter; an outlet end of the heating pipe of the steam-powder mixing pipe is connected to the recovered steam heat exchanger through a heating pipe outlet valve of the steam-powder mixing pipe; recovered steam passes through the recovered steam heat exchanger, and returns to the steam generator through the condensate recovery pipe; and the condensate filter is connected to the condensate recovery pipe, and is located between the recovered steam heat exchanger and the steam generator.

9. The continuous differential-pressure steam sterilization method for the powder according to claim 6, wherein in the continuous differential-pressure steam sterilization system for the powder, the Laval nozzle comprises a main body made of food-grade stainless steel and an inner lining made of Teflon or ceramic.

10. The continuous differential-pressure steam sterilization method for the powder according to claim 6, wherein in the continuous differential-pressure steam sterilization system for the powder, an outlet of the primary gas-solid separation system is provided with the second spiral closed-air aspirator; an inlet of the second spiral closed-air aspirator is provided with a contact sensor; and the contact sensor is connected to a motor controller of the second spiral closed-air aspirator.

* * * * *